(12) United States Patent
Owen et al.

(10) Patent No.: US 6,867,858 B2
(45) Date of Patent: Mar. 15, 2005

(54) RAMAN SPECTROSCOPY CRYSTALLIZATION ANALYSIS METHOD

(75) Inventors: Harry Owen, Ann Arbor, MI (US); Mark Welch, West Chester, OH (US); Michael J. Pelletier, Pasadena, CA (US)

(73) Assignee: Kaiser Optical Systems, Ann Arbor, MI (US)

( * ) Notice: Subject to any disclaimer, the term of this patent is extended or adjusted under 35 U.S.C. 154(b) by 97 days.

(21) Appl. No.: 10/368,176

(22) Filed: Feb. 18, 2003

(65) Prior Publication Data

US 2004/0004714 A1 Jan. 8, 2004

Related U.S. Application Data

(60) Provisional application No. 60/357,457, filed on Feb. 15, 2002.

(51) Int. Cl.[7] .................................................. G01J 3/44

(52) U.S. Cl. ........................ 356/301; 356/302; 436/4

(58) Field of Search ................................ 356/301, 302, 356/30; 436/4, 171

(56) References Cited

U.S. PATENT DOCUMENTS 6,465,255 B1 * 10/2002 Asay et al. ................. 436/164

\* cited by examiner

Primary Examiner—Layla G. Lauchman
(74) Attorney, Agent, or Firm—Gifford, Krass, Groh, Sprinkle, Anderson & Citkowski, PC (57) ABSTRACT

A method of monitoring sample crystallization from a solution. The method includes the collection of multiple Raman spectra from a sample dissolved in a solvent as a function of time and under conditions promoting crystallization. Within each of the multiple Raman spectra, a first signal is identified corresponding to the sample associated with the solvent. A second signal corresponding to the sample in a microcrystallite state is also identified. Thereafter, the intensity of the multiple Raman spectra are measured for an increase relating to formation of the sample in a microcrystallite state. A method of monitoring sample crystallization from a solution as a function of turbidity is also disclosed. The method includes the collection of multiple Raman spectra from a sample dissolved in a solvent as a function of time under conditions promoting crystallization. A decrease in intensity is measured across the multiple Raman spectrum over time, the intensity decrease associated with macroscopic crystallization opacity. The decrease in intensity is finely correlated with the onset of macroscopic crystallization of the sample from the solvent.

19 Claims, 10 Drawing Sheets

RAMAN SPECTROSCOPY CRYSTALLIZATION ANALYSIS METHOD

RELATED APPLICATION

This application claims priority of U.S. Provisional Application Ser. No. 60/357,457 filed Feb. 15, 2002, which is incorporated herein by reference.

FIELD OF THE INVENTION

The present invention generally relates to a method for monitoring a crystallization process, and in particular to a method of monitoring crystallization with a conventional Raman spectroscopy apparatus.

BACKGROUND OF THE INVENTION

Many pharmaceutical and industrial processes rely upon crystallization to assure purity and polymorphic control of a product. Representative of such processes are selective polymorphic crystallization of progesterone and separation of hydrocarbon isomers. For such processes, the attainment of a specified level of purity is desired that does not vary between batches or over time in a continuous production mode. While it is conventional to utilize a turbidity meter to measure the amount of light scattering associated with the progression of crystallization, this has limited applicability owing to the fact that most of the critical events controlling crystallization have already occurred by the time crystallites are of a sufficient size to scatter light. This, coupled with lack of additional sampling ports available to monitor especially in microreaction vessels, has left many crystallization reactions lacking adequate in situ monitoring.

There exists a number of analytical methods for offline sampling of crystal analysis regarding polymorphism and crystal quality. These methods include differential scanning calorimetry, x-ray diffraction, infrared spectroscopy and Raman spectroscopy. Unfortunately, offline sampling cannot provide information in a timely manner to adjust crystallization parameters to drive the process toward a desired result. Additionally, offline sampling is not necessarily indicative of material within a reaction vessel as polymorphic transformations and crystal growth may continue during sample filtration, drying and analytical sample preparation.

While both infrared absorption spectroscopy and Raman spectroscopy are potentially useful to monitor chemical and physical processes in real time, Raman spectroscopy affords certain advantages relative to infrared absorption spectroscopy including a weak Raman signal associated with water and other important crystallization solvents thereby facilitating true in situ crystallization monitoring. Additionally, Raman spectroscopy is more amenable to remote sensing via fiber optics. Thus, there exists a need for a method of monitoring sample crystallization from a solution in real time by way of Raman spectroscopy that affords at least turbidity meter information and ideally information about microcrystallites before appreciable light scattering occurs.

SUMMARY OF THE INVENTION

A method of monitoring sample crystallization from a solution is detailed herein. The method includes the collection of multiple Raman spectra from a sample dissolved in a solvent as a function of time and under conditions promoting crystallization. Within each of the multiple Raman spectra, a first signal is identified corresponding to the sample associated with the solvent. A second signal corresponding to the sample in a microcrystallite state is also identified. Thereafter, the intensity of the multiple Raman spectra are measured for changes, and often increases relating to formation of the sample in a microcrystallite state.

A method of monitoring sample crystallization from a solution as a function of turbidity is also disclosed. The method includes the collection of multiple Raman spectra from a sample dissolved in a solvent as a function of time under conditions promoting crystallization. A decrease in intensity is measured across the multiple Raman spectrum over time, the intensity decrease associated with macroscopic crystallization opacity. The change, and often decrease in intensity is finely correlated with the onset of macroscopic crystallization of the sample from the solvent.

BRIEF DESCRIPTION OF THE DRAWINGS

FIGS. 2(a) and (b) are Raman spectra of (a) the solvent and (b) the product crystals isolated from the tribehenin crystallization reaction of FIG. 1. The bands designated with an asterisk are associated with the window of an immersion optic.

DETAILED DESCRIPTION OF THE PREFERRED EMBODIMENTS

The present invention has utility as a method of monitoring crystallization progression in situ. The present invention is operative to monitor any crystallization reaction characterized by Raman scattering intensity. Crystallization from solution where a variety of materials is monitored according to the present invention for material illustratively including proteins, carbohydrates, fatty acid compounds, nucleotides, enzymes, other organic molecules, organometallic compounds, inorganic compounds, and crystallite inclusions within glasses. The present invention manipulates Raman spectrum collected over time from a sample dissolved in a solvent under conditions promoting crystallization to extract opacity information and thereby yield information comparable to a turbidity meter. Further, Raman spectroscopy also is capable of providing information about interaction between sample units that have become self-associated and as such are in a pre-nucleation or microcrystallite state. Further, some information regarding the size and shape of crystallites is also derived from Raman spectra according to the present invention.

Crystallization characterization and control are principal concern in many industries where control of crystallization conditions, driving crystallization to a particular polymorph, and controlling size are all of concern. The monitoring of a crystallization reaction is equipment intensive and a variety of probes must naturally coexist in situ with the reaction volume. The use of multiple small volume crystallization reactors, especially for high value substances, afford a number of advantages to increase reaction throughput and minimize raw material usage. Such crystallization reaction systems are particularly well suited to adopt the inventive methodology.

The present invention is characterized by the transmission of a monochromatic light signal of a wavelength of between 208 and 1300 nanometers and preferably between 350 and 1064 nanometers into a crystallization reaction volume. A diffused polychromatic signal is recovered from the light intersecting volume of the crystallization reaction is recovered corresponding to the Raman effect between 100 and 3500 wave numbers. It is appreciated that the spectral regions of interest are largely dictated by the characteristics of the crystallization sample material in solvated and crystalline forms. The diffused polychromatic signal is sent to a multi-channel spectrometer to deliver the corresponding Raman spectrum which is stored for subsequent comparison to other spectra collected during the crystallization reaction over time.

Raman detection is ordinarily used to determine the amount of each crystal form present in a reaction mixture during a crystallization or an annealing phase. Crystallization tends to reduce the detected Raman intensity because a solution containing crystals is more opaque than the corresponding transparent solution containing solvated crystal subunits present prior to formation of crystals. The reduction in Raman intensity associated with crystal formation is typically removed mathematically from Raman spectra through the use of some type of normalization routine, such as an internal standard. The removal of deleterious Raman intensity change associated with the various stages of crystal formation and dissolution aid in the extraction of polymorphic crystal information from a series of Raman spectra. In contrast, the present invention retains what had previously been considered deleterious Raman intensity change information associated with opacity changes during crystallization to extract information about the crystallization process. As a result, the Raman intensity of spectral features provide turbidity probe type information. Preferably, the Raman spectral feature is a solvent band. Extraction of turbidity probe information from Raman spectra collected during the course of a crystallization experiment affords additional information than is conventionally collected from Raman spectra independent of additional turbidity meter equipment and the need for a turbidity meter port on the crystallization reaction vessel.

Additionally, pre-association of sample species prior to nucleation and crystallization nuclei present prior to the formation of crystals are metastable structures that are dimensionally sufficiently small that they do not significantly change the opacity of a solution. Nonetheless, the transition from a fully solvated sample species to a self-associating pre-nucleation species, to a microcrystallite that does not appreciably interact with visible light still changes the density of the crystallization solution. Crystallization solution density change in the course of crystallization is utilized according to the present invention to note an increase in Raman intensity prior to the precipitation of crystals. The present invention relies on the change, and most often the increase of Raman intensity to monitor crystal formation in situ and essentially in real time prior to the formation of crystals having a dimension large enough to scatter visible light. Additionally, Raman scattering from certain size crystallites also affords information as to size, distribution and shape of the crystallites. It is appreciated that utilizing an increase in Raman intensity observed prior to precipitation of crystals shows their most intense signals in instances where the bulk density of crystals formed during a crystallization reaction is much greater than the bulk density of the corresponding saturated solution of sample material.

The present invention is further described with respect to the following examples. These examples are intended to be illustrative and not limiting as to the scope of the invention.

EXAMPLE 1

A RamanRxn1 analyzer (Kaiser Optical Systems, Ann Arbor, Mich.) was interfaced to a two liter reaction vessel through the use of an 18 inch long fiber optic immersion probe sealed with a sapphire window (Kaiser Optical Systems). The Raman spectra were collected using approximately 100 milliwatts of 785 nanometer laser excitation. This setup yielded a spectral resolution of approximately four wave numbers. The reaction vessel was a two liter temperature controlled reaction vessel. The reaction vessel was charged with a saturated solution of tribehenin (1,2,3-propspanetriyl ester of docosanoic acid) dissolved in an equimolar solvent mixture of cyclomethicone and dimethicone. Reaction temperature and monitoring is performed with a reaction calorimeter.

Figure 1:
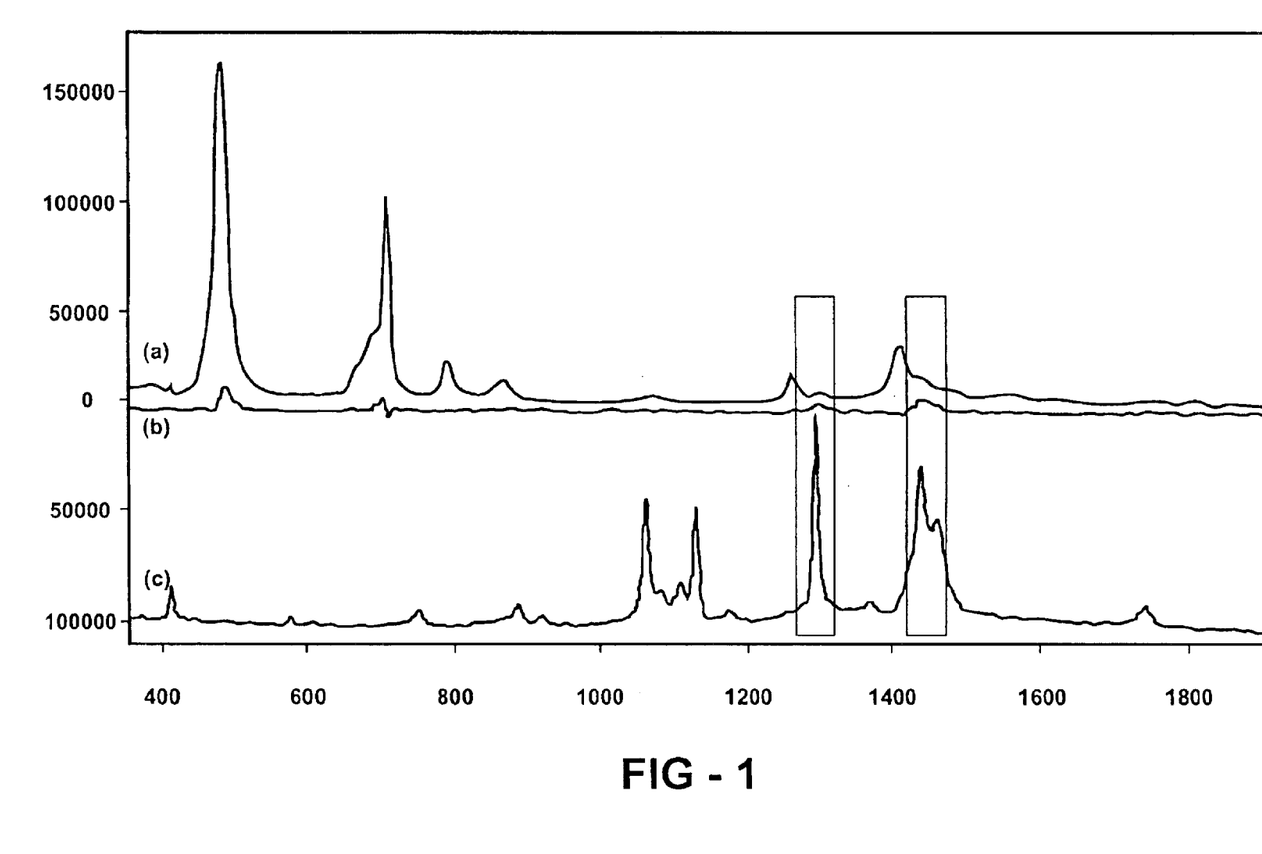
FIGS. 1(a)–(c) are Raman spectra of tribehenin dissolved in cyclomethicone and dimethicone collected in situ from a two liter glass reactor (a) just prior to crystallization temperature drop, (b) spectrum of FIG. 1(a) after solvent spectrum subtraction, and (c) tribehenin. Spectral regions of particular interest are enclosed within rectangular boxes.

Before recording any crystallization data, Raman spectra in a low wave number spectral region are collected from the reactor contents of the saturated tribehenin solution, as shown in FIG. 1(a). The spectrum is also plotted in FIG. 1 after mathematical subtraction of the solvent spectra and that of the tribehenin sample material, as shown in FIG. 1(c). The boxes shown in FIG. 1 enclose wave number spectral regions of particular analytical interest.

EXAMPLE 2

Figure 2:
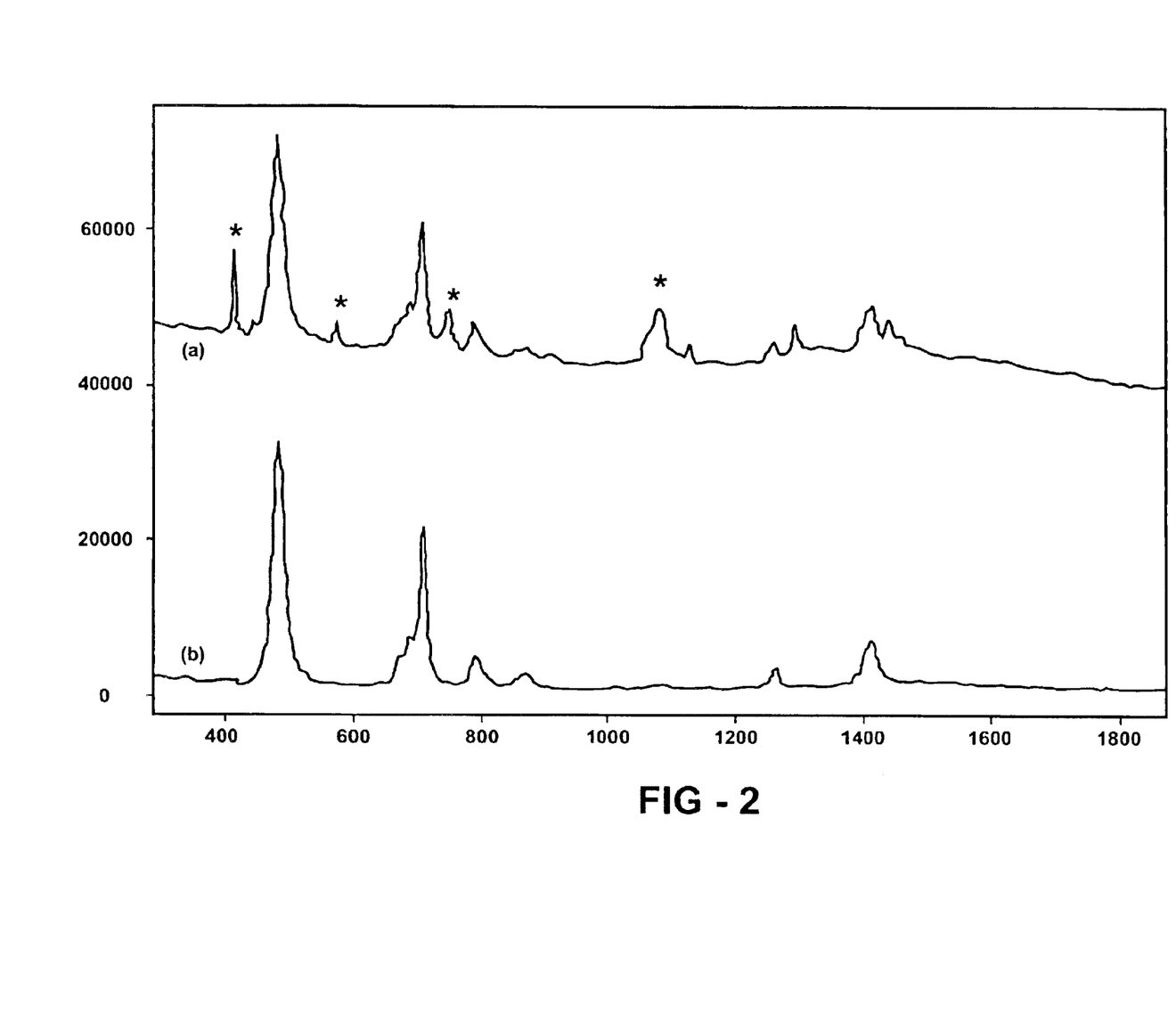
Figure 3A:
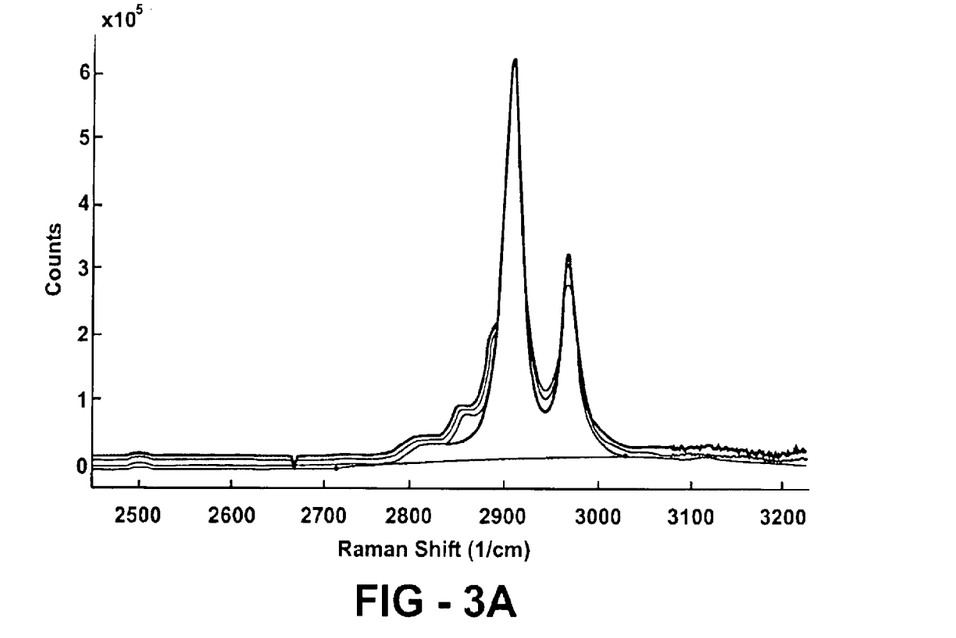
FIG. 3(a) are Raman spectra in the C—H stretching region plotted as integrated area displayed as a function of time.
Figure 3B:
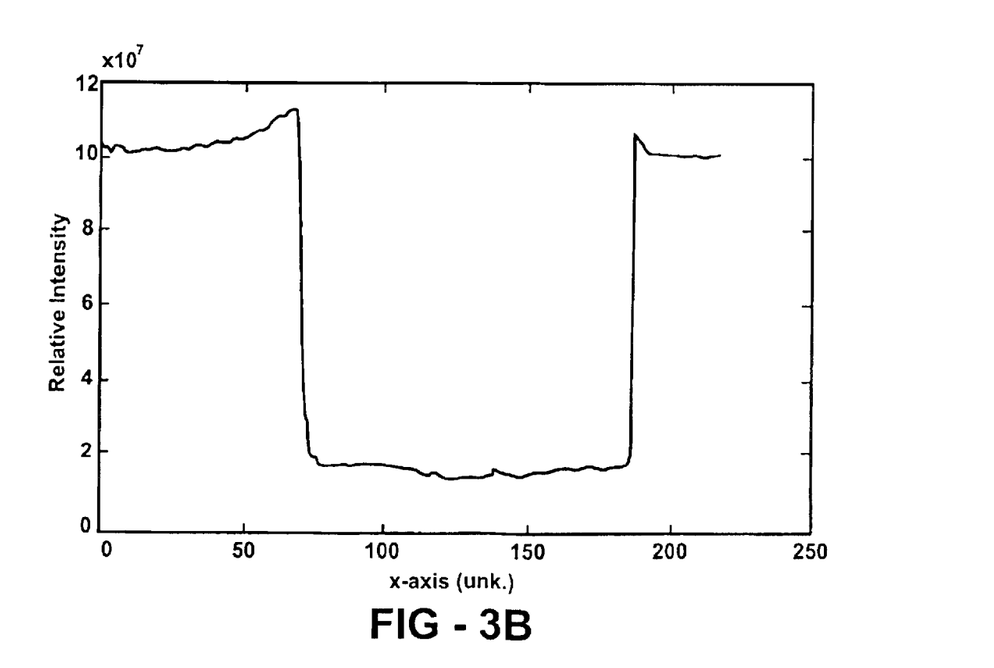
FIG. 3(b) is a plot of integrated area according to FIG. 3(a) plotted as a function of sequential spectrum number, showing a sharp drop in spectral intensity at spectrum number 70 corresponding to crystal formation and an accompanying temperature drop from 85° Celsius to 40° Celsius. The rise in spectral intensity prior to spectrum number 70 correlates to pre-nucleation phenomena while the sharp rise associated with spectrum 191 corresponds to a temperature increase back to 85° Celsius.
Figure 4:
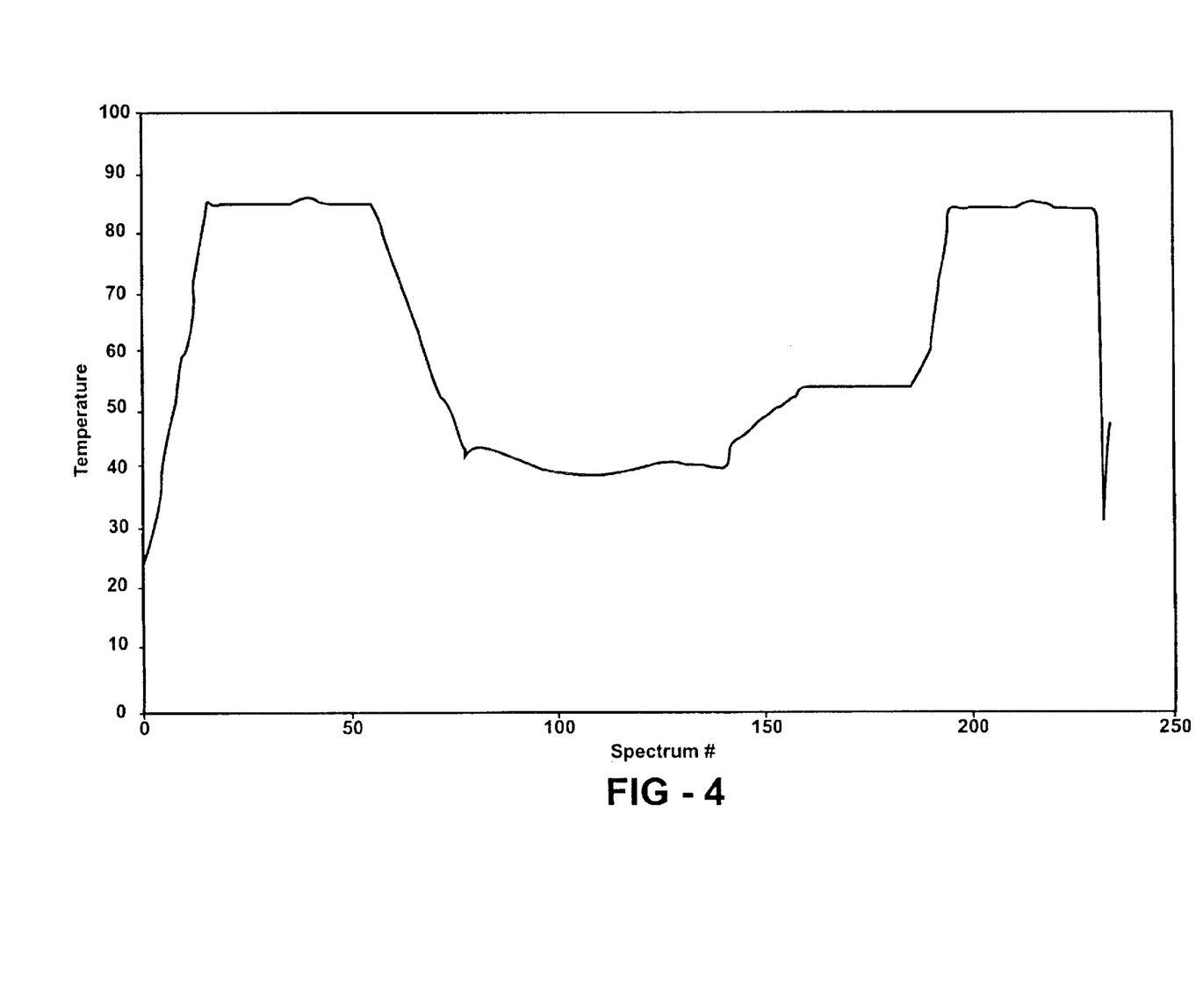
FIG. 4 is a temperature profile plotted as a function of spectrum number according to FIGS. 3(a) and 3(b).

Raman spectra are collected at one minute intervals, with each recorded spectrum being a sum of five spectra each integrated for 10 seconds. The temperature profile is sampled in conjunction with the Raman spectrum collection rate using the reaction calorimeter and thermal controller, as shown in FIG. 4. The Raman spectra of the tribehenin product isolated from the reaction are shown in FIG. 2(a) while that of the solvent is depicted in FIG. 2(b). Those spectral bands of the tribehenin product delineated with an asterisk are associated with the sapphire window of the immersion optic. Integrating baseline subtracted peak area in the C—H stretch region of the tribehenin Raman spectrum from 2730 to 3055 wave numbers following baseline correction as shown in FIG. 3(a) is plotted as a relative intensity as a function of scan number in FIG. 3(b). An increase in integrated peak area is noted most dramatically in spectrum numbers 48–70 and corresponds to pre-nucleation tribehenin-tribehenin molecular interactions and microcrystallite formation. The step function observed relative intensity at spectrum number 70 corresponds to a reaction vessel temperature drop from 85° Celsius to 40° Celsius. The sharp rise in spectrum 191 of FIG. 3(b) corresponds to a temperature increase back to the set point of 85° Celsius.

Figure 5:
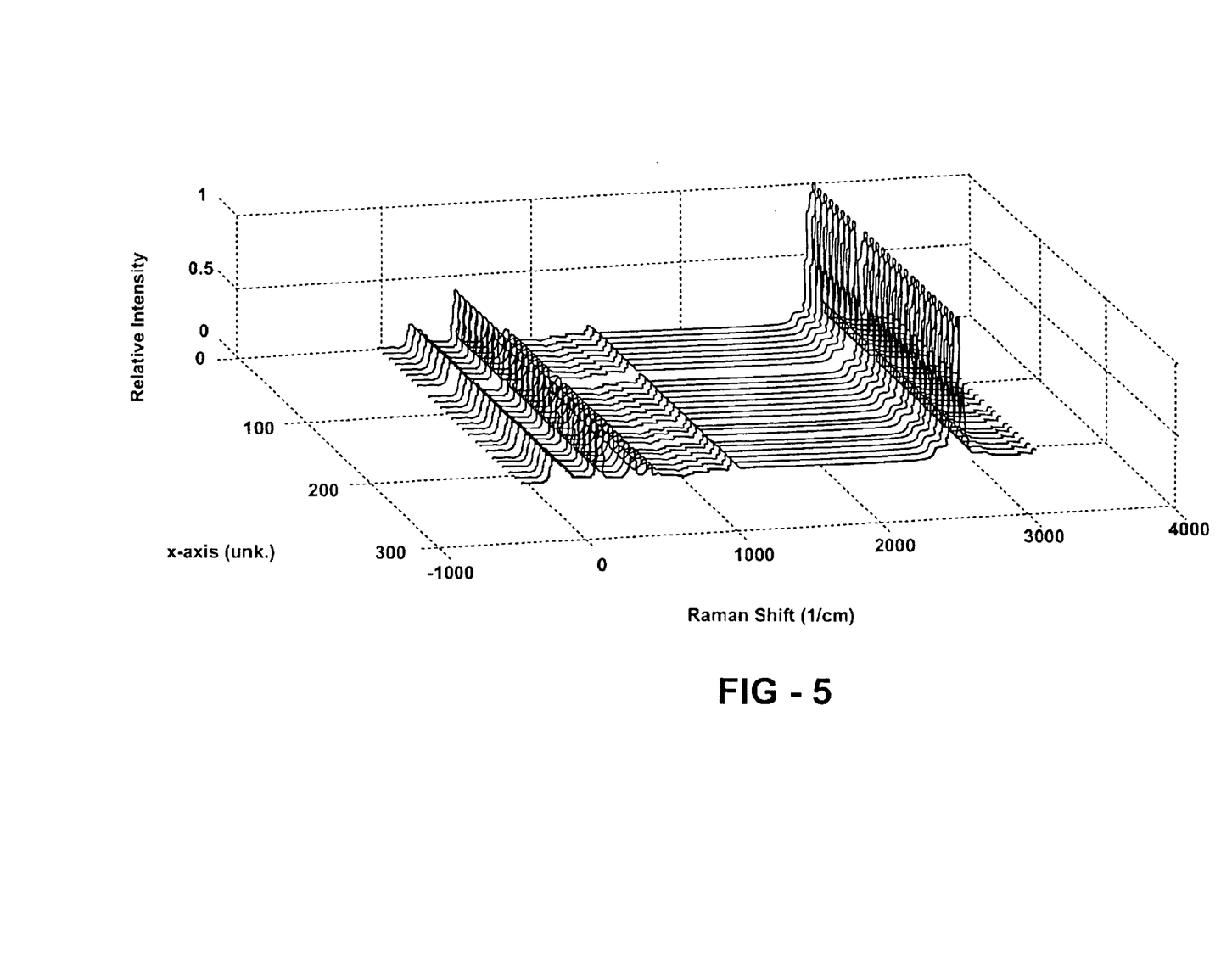
FIG. 5 are Raman spectra collected during the tribehenin crystallization reaction displayed as a waterfall plot where intensity has been normalized to the area of the C—H stretching region as a function of spectrum number according to FIG. 3.
Figure 6:
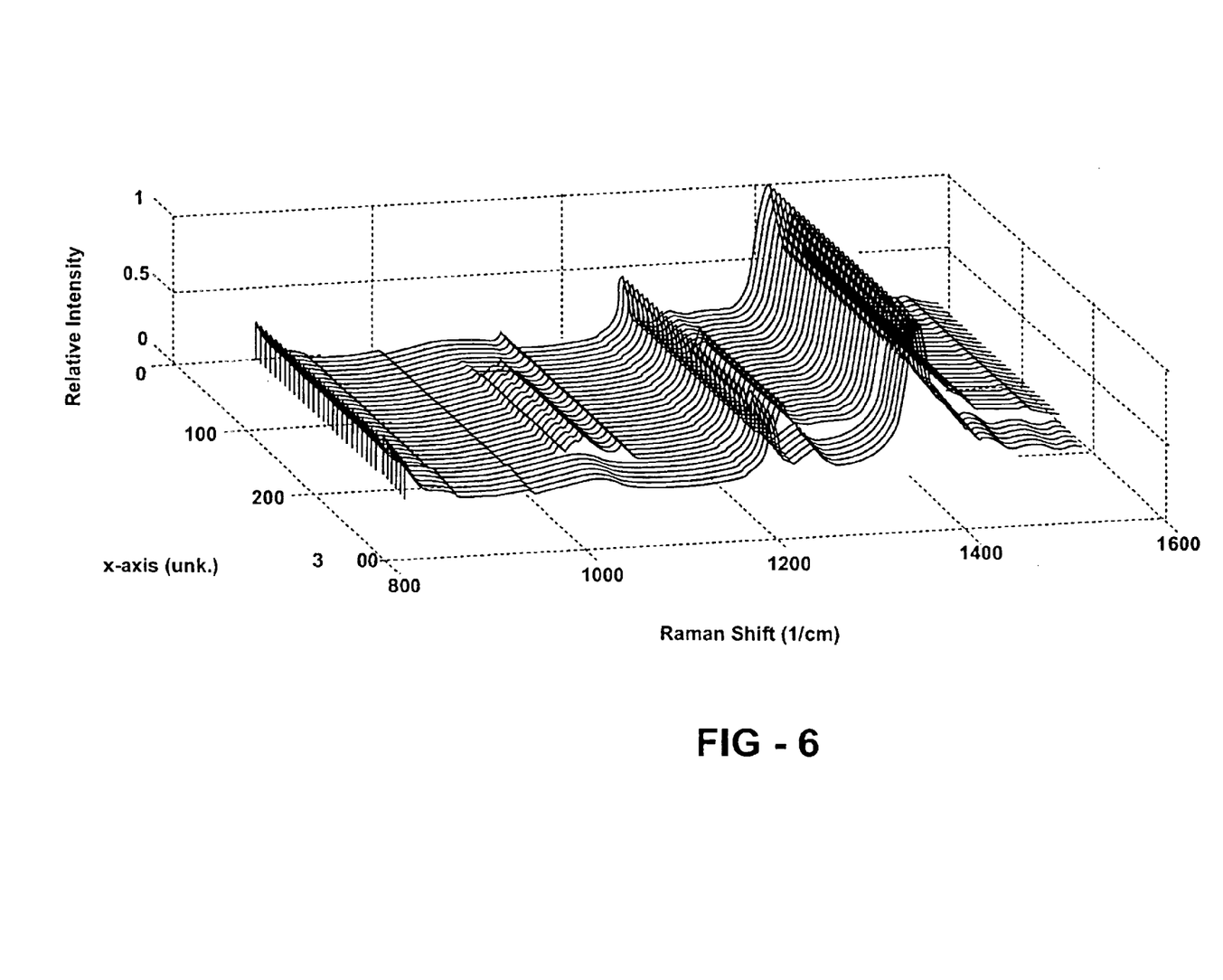
FIG. 6 is a magnified region of FIG. 5 extending from 825 to 1600 wave numbers.
Figure 7:
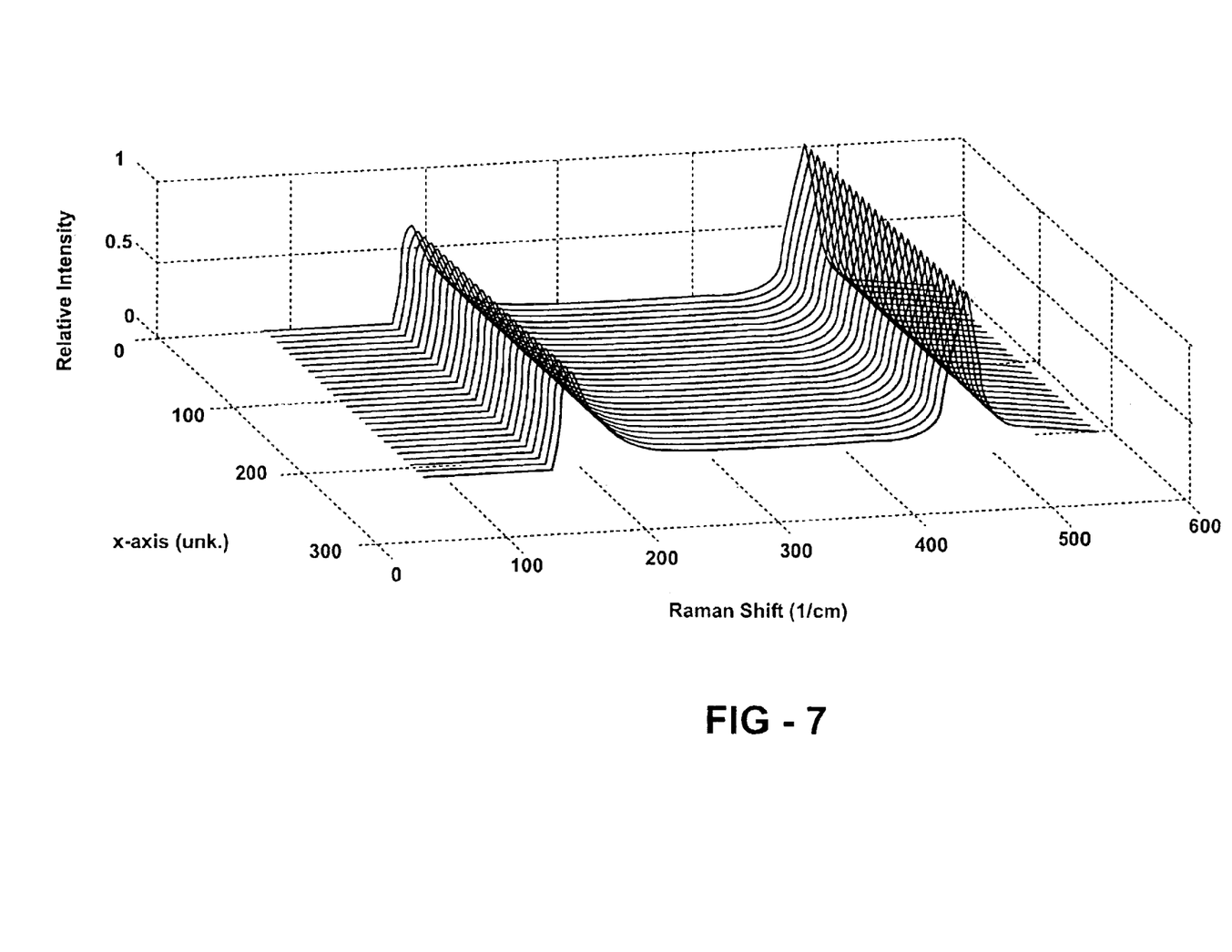
FIG. 7 is a magnified region of the spectra depicted in FIG. 5 showing the region from 80 to 590 wave numbers.

FIGS. 5–7 show the Raman spectra collected in the course of tribehenin crystallization where the wave number scale varies within the figures.

Figure 8A:
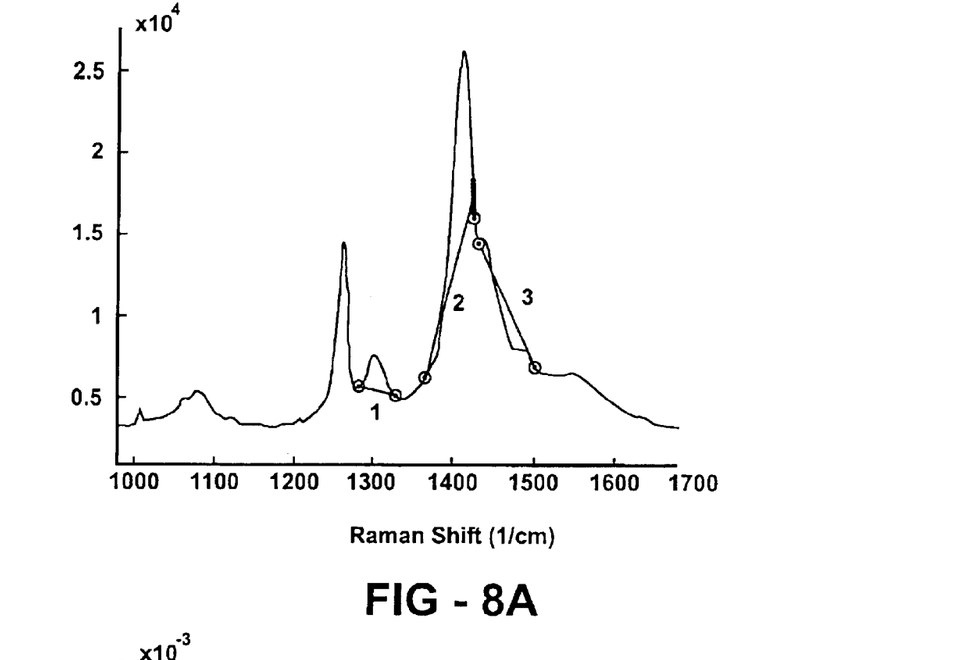
FIG. 8(a) is a Raman spectrum showing the C—H bending region of tribehenin where numerals 1–3 represent integration endpoints.
Figure 8B:
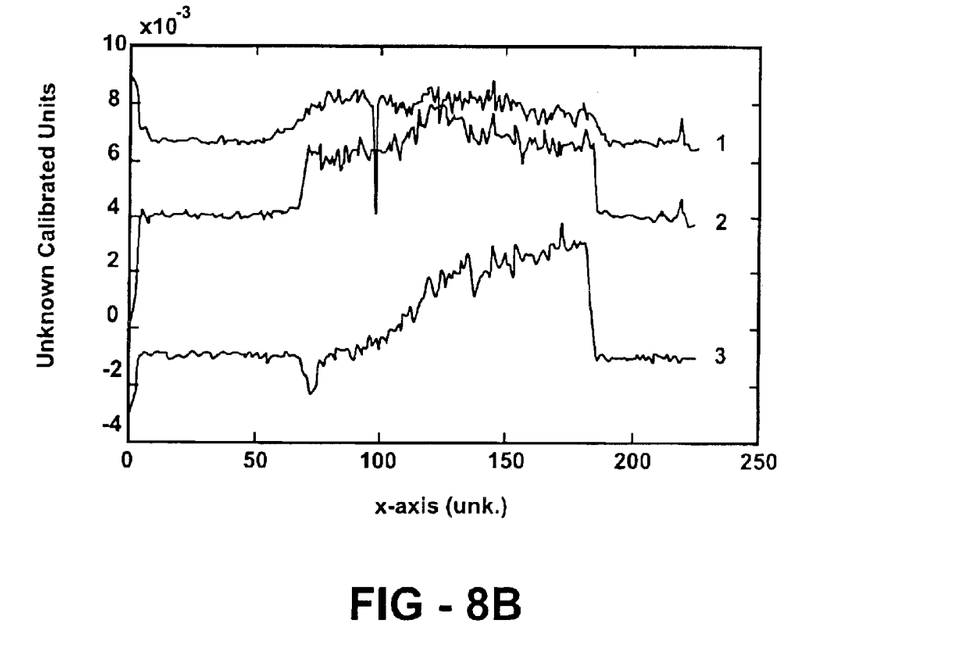
FIG. 8(b) are integrated areas of the tribehenin spectrum corresponding to integration areas (1–3) of FIG. 8(a) as a function of spectrum number according to the preceding figures noting a change in the tribehenin spectra during the time the reactor is at a lower temperature of 40° Celsius between spectrum 71 and spectrum 190.
Figure 9:
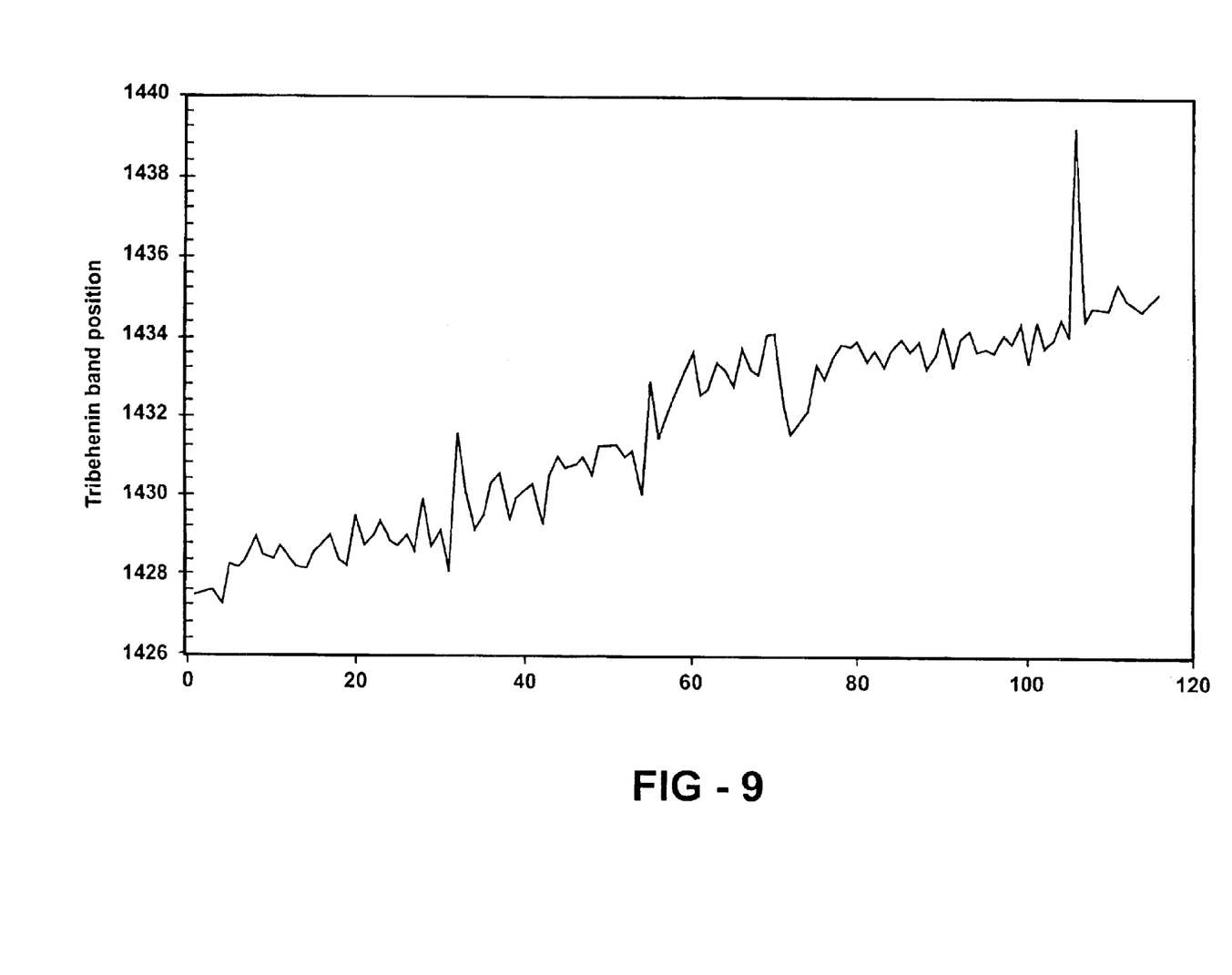
FIG. 9 is a plot of tribehenin band position in wave numbers during the time the reaction mixture is held at a lower temperature of 40° Celsius, where the X axis origin corresponds to spectrum 71 of the preceding figures.
Figure 10A:
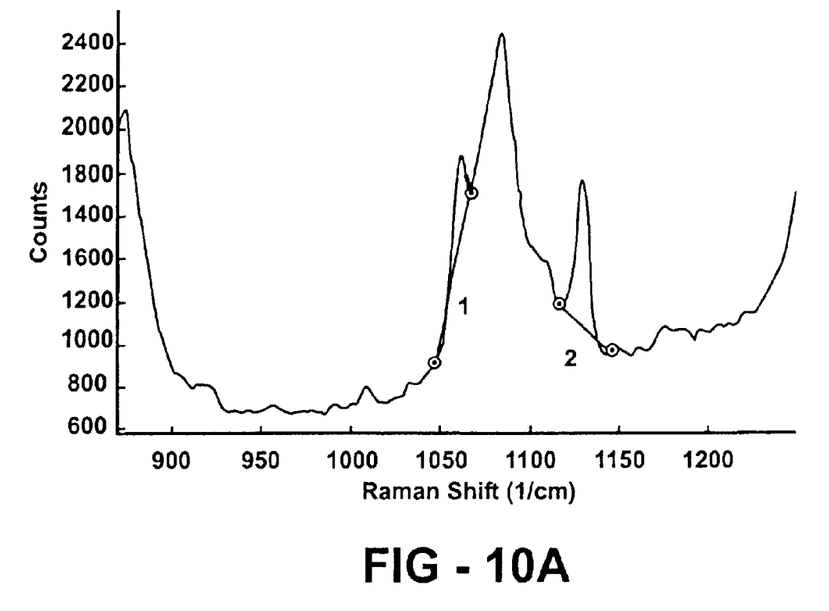
FIG. 10(a) is the Raman spectrum of type tribehenin showing the bands near 1062 wave numbers (1) and 1130 wave numbers (2) that disappear upon tribehenin dissolution.
Figure 10B:
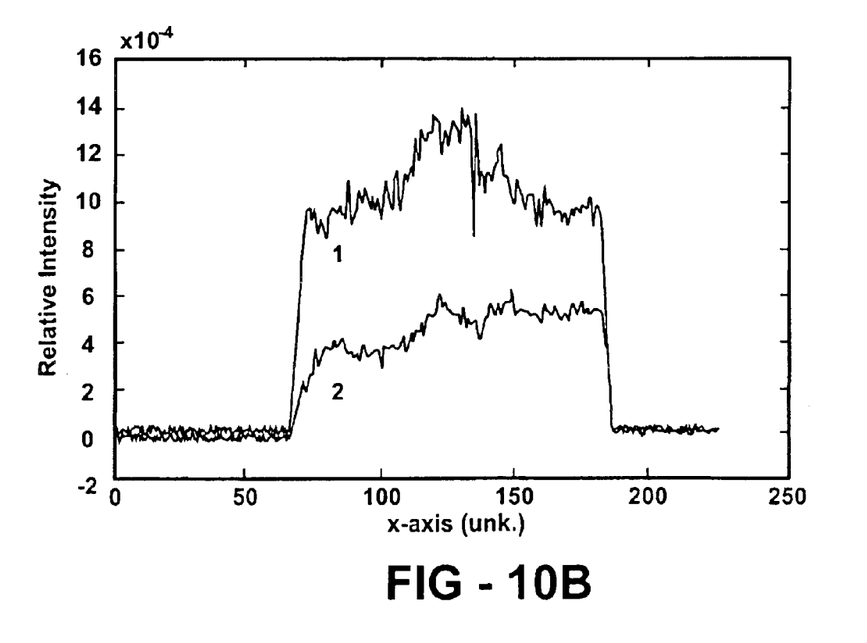
FIG. 10(b) is a plot of integrated intensity across integration endpoints (1) and (2) according to FIG. 10(a) as a function of spectrum number.

The Raman spectra of tribehenin in the C—H bending region shows a demonstrable change in intensity while the reactor is held at the lower temperature of 40° Celsius noted in FIG. 8(b) between spectrum 71 and 190. This is especially true based on the integration between spectral points denoted as, 3 in FIGS. 8(a) and 8(b). A plot of the tribehenin band position in the C—H bending region while the reaction vessel is at 40° Celsius shows a linear change in band position with spectrum number 71 normalized in FIG. 9 as the X axis starting point. Additionally, the Raman spectrum of tribehenin shows two distinct bands centered around 1062 wave numbers and 1130 wave numbers, as shown as a waterfall plot clearly in FIG. 6, as well as in FIG. 10(a). With solvent dissolution, the tribehenin bands at 1062 wave numbers and 1130 wave numbers disappear where the integration endpoints shown in FIG. 10(a) as a function of scan number in FIG. 10(b).

Upon analysis of the C—H stretching region, C—H bending region and the unassigned bands at 1062 and 1130 wave numbers for tribehenin, information is provided with respect to pre-opacity modifying tribehenin-tribehenin and/ortribehin-solvent interactions, tribehenin microbe crystallite seed formation, as well as macroscopic crystal growth.

EXAMPLE 3

The experiment of Example 2 is repeated substituting brassidic anhydride (trans-13-docosanoic anhydride) for tribehenin. Brassidic anhydride is known to form needles upon crystallizing from ethanol and plates upon crystallizing from diethyl ether. The experiment of Example 2 is repeated with brassidic anhydride dissolved in anhydrous ethanol and repeated in anhydrous diethyl ether. Brassidic anhydride has a melting temperature of about 64° Celsius and as such the thermal profiles of Example 2 were reproduced. A comparison of Raman spectra data sets for brassidic anhydride crystallized from ethanol and diethyl ether spectral differences are noted that correlate to the differential cross section of the respective crystalline forms. Where the differential cross section is given by $$\frac{\partial \sigma}{\partial \Omega}(Q) = N_p V_p^2 (\Delta \delta)^2 P(Q) S(Q) + B_{inc}$$

where $N_p$ is the number concentration of scattering bodies (given the subscript "p" for "particles"), $V_p$ is the volume of one scattering body, $(\Delta \delta)^2$ is the square of the difference in contrast, P(Q) is a function known as the form or shape factor, S(Q) is the interparticle structure factor, Q is the modulus of the scattering vector and $B_{inc}$ is the (isotropic) incoherent background signal. $(M\sigma/M\Omega)(Q)$ has dimensions of $(length)^{-1}$ and is normally expressed in units of $cm^{-1}$. (H. C. van de Hulst, "Light Scattering by Small Particles", John Wiley, 1957 M. Kerker, "The Scattering of Light and other Electromagnetic Radiation", Academic Press, 1969 O. Glatter; O. Kratky (editors), "Small Angle X-ray Scattering", Academic Press, 1982. Analyzing the Raman spectrum with known parameters of the crystallization reaction, Raman spectral features are noted that correlate to each crystalline form.

EXAMPLE 4

Since Raman spectroscopy is able to discern between samples of the same sample volume and varying surface area, the present invention is applicable to determining mean particle size for a given particle shape. By way of example, a 100 micron particle has a surface area of 31,400 square microns and a total volume of 524,000 cubic microns; this is on contrast to 1000 particles, each having a diameter of 10 microns, a surface area of 314,000 square microns, and a volume of 524,000 cubic microns. An experiment in which monodisperse polystyrene spheres in water having the above relative concentrations and sizes are measured with the optical apparatus of Example 1. The sample containing few, 100 micron particles showed an increase in turbidity that correlated to a longer cord length the sample relative to the 10 micron particle sample.

Any patents or publications mentioned in the specification are indicative of the levels of those skilled in the art to which the invention pertains. These patents and publications are herein incorporated by reference to the same extent as if each individual patent or publication was specifically and individually indicated to be incorporated by reference.

One skilled in the art will readily appreciate that the present invention is well adopted to afford the intended utility. The foregoing description is illustrative of particular embodiments of the invention, but is not meant to be a limitation upon the practice thereof. The following claims, including all equivalents thereof, are intended to define the scope of the invention.

What is claimed is:

1. A method of monitoring sample crystallization from a solution comprising the steps of:
    collecting a plurality of Raman spectra from a sample dissolved in a solvent as a function of time under conditions promoting crystallization;
    identifying within each of said plurality of Raman spectra a first signal corresponding to said sample associated with said solvent and a second signal corresponding to said sample in a microcrystalline state; and
    measuring intensity changes of each of said Raman spectra for an intensity change relating to formation of said sample in a microcrystalline state.

2. The method of claim 1 wherein the intensity changes measured are increases in intensity.

3. The method of claim 1 wherein said plurality of Raman spectra are collected with a fixed wavelength.

4. The method of claim 1 wherein said sample is selected from a group consisting of: proteins, carbohydrates, fatty acid compounds, nucleotides, enzymes, other organic molecules, organometallic compounds, inorganic compounds, and crystallite inclusions within glasses.

5. The method of claim 1 wherein the condition promoting crystallization is a change in temperature.

6. The method of claim 1 wherein the condition promoting crystallization is a solvent volume.

7. The method of claim 1 wherein the condition promoting crystallization is an addition of antisolvent.

8. The method of claim 1 further comprising a step of identifying a third signal corresponding to said sample self-associating in a prenucleation state.

9. The method of claim 5 further comprising a step of measuring a decrease in a Raman spectra band for said plurality of Raman spectra over time, said decrease associated with macroscopic crystallization opacity.

10. The method of claim 6 further comprising a step of correlating said intensity changes with an onset of macroscopic crystallization of said sample from said solvent.

11. The method of claim 1 wherein said plurality of Raman spectra are collected by way of an immersion optic.

12. A method of monitoring sample crystallization from a solution comprising the steps of:

collecting a plurality of Raman spectra from a sample dissolved in a solvent as a function of time under conditions promoting crystallization;

measuring a decrease in a band intensity for said plurality of Raman spectra over time, said decrease associated with macroscopic crystallization opacity; and correlating said decrease in band intensity with an onset of macroscopic crystallization of said sample from said solvent.

13. The method of claim 12 wherein said plurality of Raman spectra are collected with a fixed wavelength.

14. The method of claim 12 wherein said sample is selected from a group consisting of: proteins, carbohydrates, fatty acid compounds, nucleotides, enzymes, other organic molecules, organometallic compounds, inorganic compounds, and crystallite inclusions within glasses.

15. The method of claim 12 wherein the condition promoting crystallization is a change in temperature.

16. The method of claim 12 wherein said plurality of Raman spectra are collected by way of an immersion optic.

17. The method of claim 12 wherein measurement of the decrease in band intensity is independent of mathematical removal through normalization.

18. The method of claim 12 further comprising a step of correlating a Raman spectrum from said plurality of Raman spectra with a known shape factor for said sample in a crystalline form.

19. A method for crystallizing a compound which comprises dissolving a compound in a solvent; promoting crystallization of said sample from said solvent by modifying a condition selected from the group consisting of a decrease in solvent volume and a decrease in solvent temperature; and monitoring sample crystallization according to claim 1.

* * * * *